(12) United States Patent
Renault

(10) Patent No.: US 7,784,144 B2
(45) Date of Patent: Aug. 31, 2010

(54) ELECTRIC TOOTHBRUSH HEAD REPLACEMENT SYSTEM AND METHOD

(76) Inventor: Greg Renault, P.O. Box 832, La Jolla, CA (US) 92038

(*) Notice: Subject to any disclaimer, the term of this patent is extended or adjusted under 35 U.S.C. 154(b) by 122 days.

(21) Appl. No.: 11/495,291

(22) Filed: Jul. 27, 2006

(65) Prior Publication Data

US 2008/0028587 A1    Feb. 7, 2008

(51) Int. Cl.
  *A46B 7/04* (2006.01)
  *A61C 17/20* (2006.01)
(52) U.S. Cl. .................. 15/257.01; 15/176.6; 15/167.1
(58) Field of Classification Search ............... 15/167.1, 15/176.6, 22.1, 257.01, 176.1, 176.2
See application file for complete search history.

(56) References Cited

U.S. PATENT DOCUMENTS

| 1,692,980 | A |   | 11/1928 | Farmer |  |
|---|---|---|---|---|---|
| 2,834,975 | A |   | 5/1958 | Perwas |  |
| 5,247,716 | A | * | 9/1993 | Bock | 15/22.1 |
| 5,263,218 | A |   | 11/1993 | Giuliani et al. |  |
| 5,546,624 | A |   | 8/1996 | Bock |  |
| 5,987,681 | A |   | 11/1999 | Hahn et al. |  |
| 6,446,294 | B1 |   | 9/2002 | Specht |  |
| 2003/0226223 | A1 | * | 12/2003 | Chan | 15/22.2 |
| 2005/0273951 | A1 | * | 12/2005 | Karl | 15/22.1 |

OTHER PUBLICATIONS

International Search Report for PCT/US07/74489, International Searching Authority, Sep. 2, 2008, pp. 1-4.

* cited by examiner

*Primary Examiner*—David B Thomas
(74) *Attorney, Agent, or Firm*—Samuel M. Freund; Cochran Freund & Young LLC

(57) ABSTRACT

A system and method for enabling the replacement of electric toothbrush heads on toothbrush models that require users to replace the entire toothbrush head assembly is described. Toothbrush head assemblies typically include much more than a simple toothbrush head, for example, a shank attached to magnets and a housing for coupling the shank to the toothbrush base. The present invention therefore permits the replacement of worn out toothbrush heads instead of entire toothbrush head assembly that includes many parts that have not worn out. The system includes tools for separating an existing toothbrush head from a shank and replacement toothbrush heads having new bristles that couple with the shank or the head assembly of a particular toothbrush model.

14 Claims, 5 Drawing Sheets

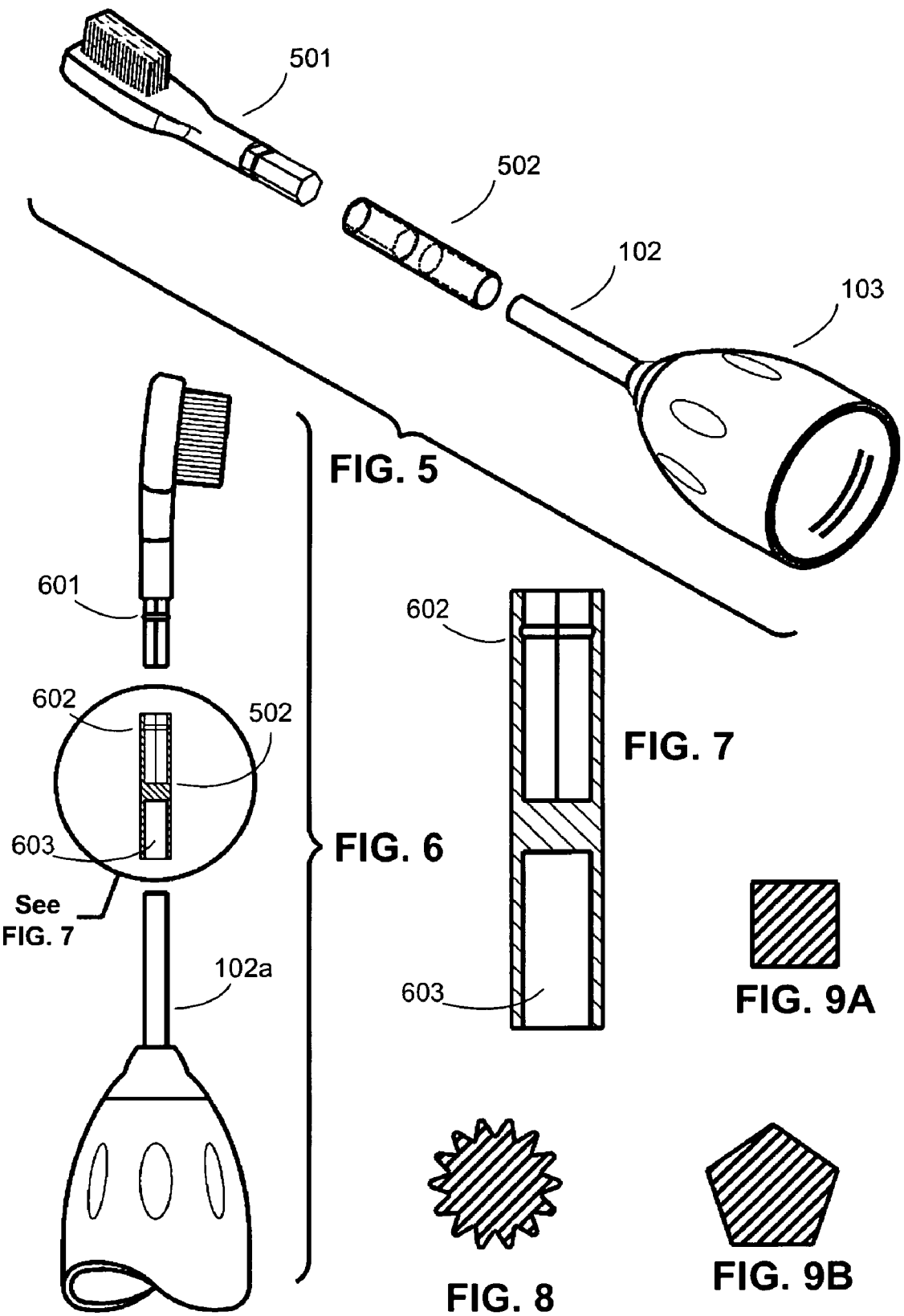

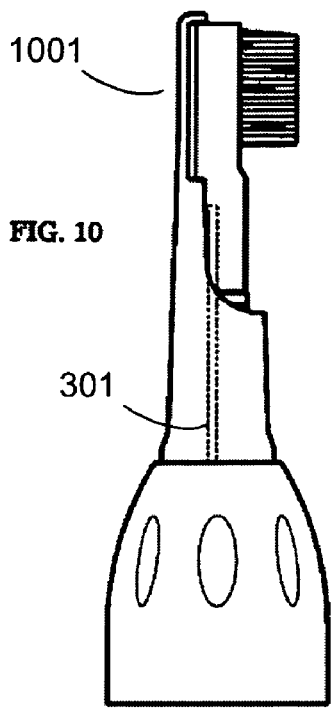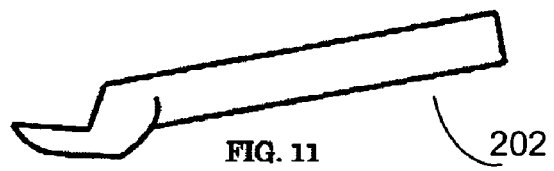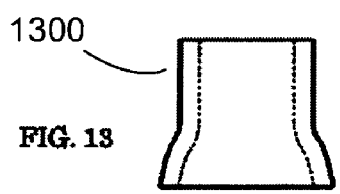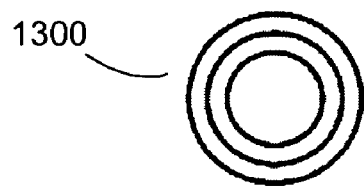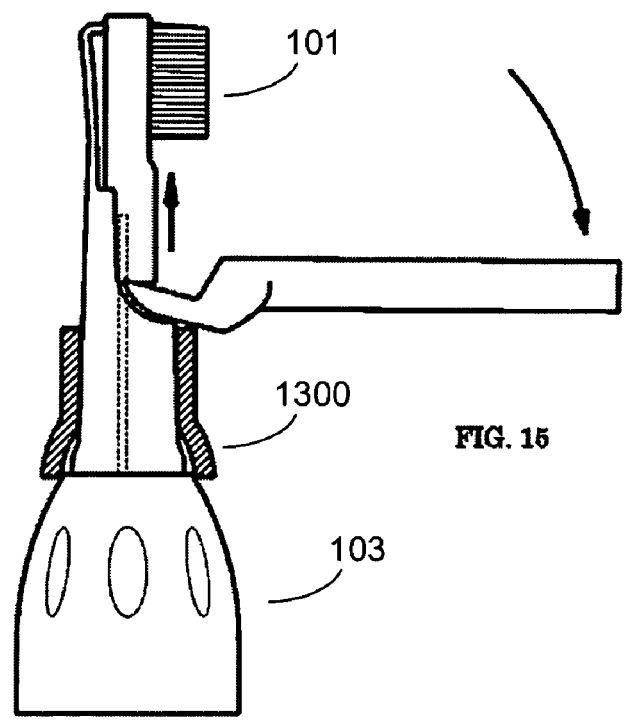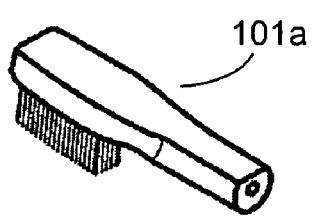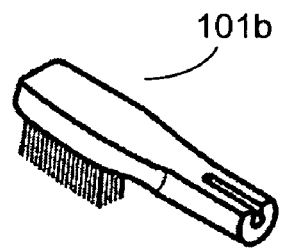

FIG. 19
FIG. 20
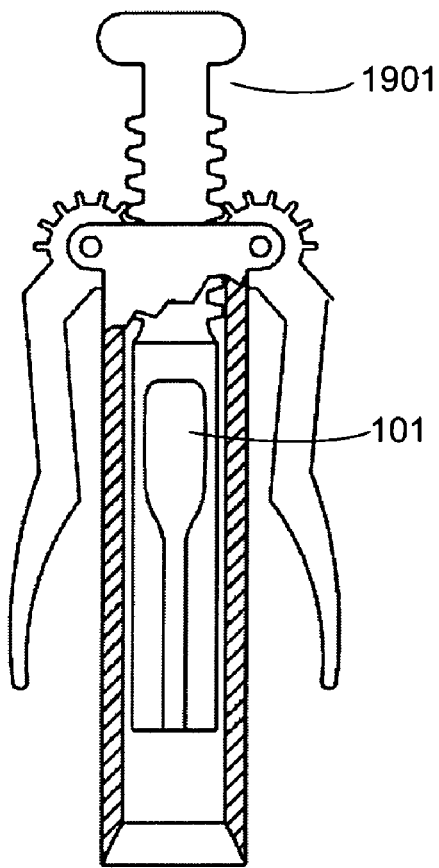
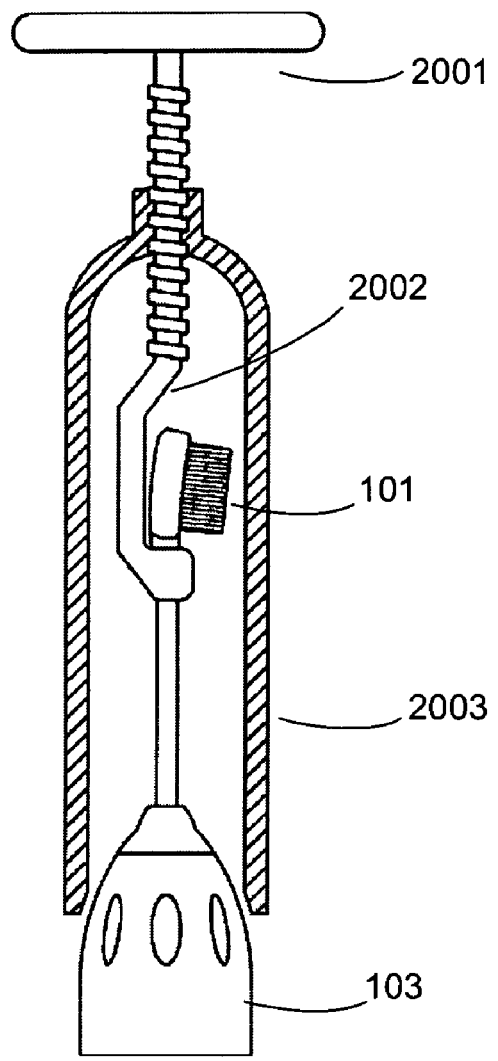
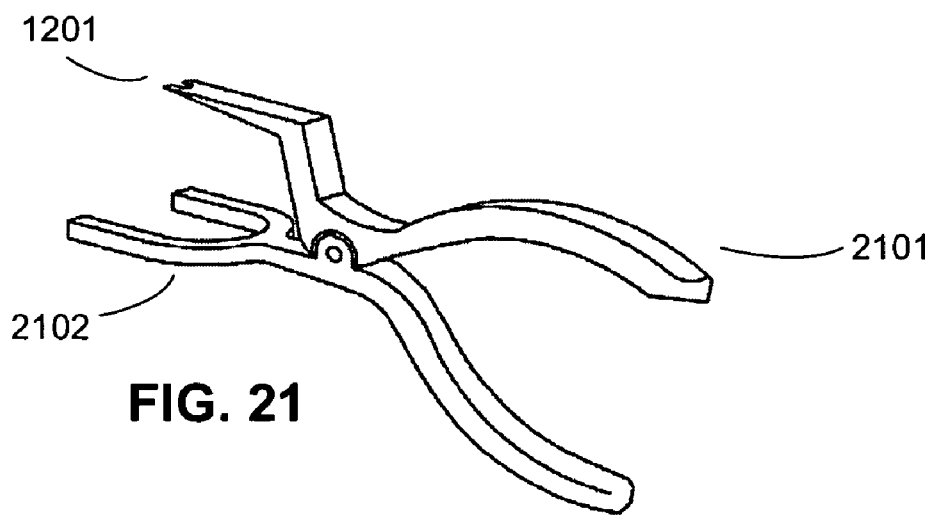
FIG. 21

ELECTRIC TOOTHBRUSH HEAD REPLACEMENT SYSTEM AND METHOD

BACKGROUND OF THE INVENTION

1. Field of the Invention

Embodiments of the invention described herein pertain to the field of electrical toothbrushes. More particularly, but not by way of limitation, one or more embodiments of the invention enable electric toothbrush head replacement on models that require users to replace entire toothbrush head assemblies.

2. Description of the Related Art

Existing electric toothbrush apparatus fall into two general classes, those that allow a user to simply change a toothbrush head, and those that do not. Certain manufacturers make more money by selling entire head assemblies including shank, housing and magnets for example that the user must replace. The head assemblies include much more than a simple toothbrush head and many of the parts that are replaced when replacing a toothbrush head are not worn out. Although selling entire head assemblies may increase the manufacturer's margin, this practice of selling more than is needed is wasteful, environmentally unfriendly and more costly to the user. Furthermore, to practice good oral hygiene, the American Dental Association (ADA) recommends that one's toothbrush be replaced every three or four months, or sooner if the bristles become frayed. People are less likely to practice good oral hygiene when the replacement costs for new toothbrush heads are high and conversely more likely to replace heads when costs are low.

Electric toothbrushes such as is described in U.S. Pat. No. 1,692,980 to Farmer have existed since at least the 1920's. Later electrical toothbrushes have become cordless, have reduced size and generally increase the brushing capabilities of the electric toothbrush. All electric toothbrushes that do not allow for a user to readily replace a worn toothbrush head share the problem of long term economical use since the user generally must replace more than a simple toothbrush head when the toothbrush head becomes worn out.

U.S. Pat. No. 5,263,218 to Giuliani et al., shows in FIG. 8, detachable brush 128 (hereinafter referred to as toothbrush head) that detaches from forward end 130 of lever arm 132 (hereinafter referred to as shank) that couples with magnets 137 to form head member 134. The toothbrush head of this device is generally tightly bound with the shank. Many similar devices crimp or bond the toothbrush head using heat or injection molding to couple the toothbrush head with the shank. This does not allow for easy removal of the toothbrush head for the purpose of replacing the toothbrush head when the toothbrush head wears out.

Electric toothbrushes that do not allow for simple toothbrush head replacement but rather require a user to purchase an entire head assembly are wasteful, environmentally unfriendly and costly to use in the long run. For at least the limitations described above there is a need for an electric toothbrush head replacement system and method.

BRIEF SUMMARY OF THE INVENTION

One or more embodiments of the invention enable an electric toothbrush head replacement system and method. An electric toothbrush head assembly includes a toothbrush head, shank and housing. After the toothbrush head wears out, generally when the bristles no longer point straight out of the toothbrush head, the toothbrush head must be replaced. Proper brushing occurs when the bristles are not frayed and allow for access between the teeth for example. To avoid replacing the entire toothbrush head assembly when the toothbrush head is worn, embodiments of the invention provide at least one toothbrush head separator tool that is configured to separate a worn toothbrush head from the shank or head assembly of an electric toothbrush. Embodiments of the invention also provide at least one replacement toothbrush head that couples with the shank or head assembly so that a new toothbrush head with new bristles is coupled with the electric toothbrush. One or more embodiments of the invention may utilize a toothbrush head shank adapter to couple with a replacement toothbrush head and the shank of the electric toothbrush depending on the model.

One or more embodiments of the invention provide a bushing that varies in size depending on the particular electric toothbrush manufacture. The bushing allows for a separator tool to be used against the bushing to pry the worn toothbrush head off of the shaft or internal metal rod that holds the toothbrush head to the housing of the electric toothbrush.

One or more embodiments of the invention may provide a shank cutter that allows for the worn toothbrush head to be removed from the lower portion of the shank for example. Any type of toothbrush head separator tool configured to separate a worn toothbrush head from the shank or housing of the head assembly so that the entire head assembly does not have to be replaced to replace a worn toothbrush head is in keeping with the spirit of the invention.

One or more embodiments of the invention provide a shank adapter configured to hold a replacement toothbrush head on the shank of the head assembly. In this embodiment of the invention, regardless of the initial type of coupling between the toothbrush head and the shank, the shank is cut or the worn toothbrush head is removed from the shank so that the shank adapter may be introduced between the shank and the replacement toothbrush head.

Embodiments of the shank adapter may use any type of coupling to secure the replacement toothbrush head to the shank adapter and any type of coupling to secure the shank adapter to the lower portion of the shank. In one or more embodiments, the shank adapter is configured to hold a replacement toothbrush head with teeth or edges and may for example snap into place in the shank adapter. The opposite portion of the shank adapter may be coupled to the lower portion of the shank with glue for example or may be heated or bonded in any other manner.

Forming the shank adapter may be performed by injection molding the shank adapter to fit a given manufacturer's electric toothbrush shank. Any other method of forming the shank adapter including machining is in keeping with the spirit of the invention. Forming the replacement toothbrush head may also be accomplished by injection molding or any other type of manufacture so long as the toothbrush head includes a method for securing toothbrush head to the housing as long as the replacement toothbrush head may be utilized to brush one's teeth.

Embodiments of toothbrush head assemblies that allow for removal of the toothbrush head even if not intended for the end user to do so allow for other replacement head embodiments that are formed specific to a particular manufacturer's internal metal rod in a shank for example. In one or more embodiments of the invention, this allows for providing a separator tool and replacement toothbrush heads without requiring providing a shank adapter. As long a replacement toothbrush head securely rotates when coupled with an electric toothbrush housing, embodiments of the invention allow for replacement of worn toothbrush heads where no possibility existed.

BRIEF DESCRIPTION OF THE DRAWINGS

The above and other aspects, features and advantages of the invention will be more apparent from the following more particular description thereof, presented in conjunction with the following drawings wherein:

FIG. 5 illustrates an exploded perspective view of the head assembly with a shank adapter configured to hold a replacement toothbrush head on the shank of the head assembly.

FIG. 6 illustrates a side view of the head assembly with a shank adapter configured to hold a replacement toothbrush head on the shank of the head assembly.

FIG. 7 illustrates a side view of the shank adapter.

FIG. 8 illustrates a cross section view of a serrated embodiment of the lower portion of the replacement toothbrush head.

FIG. 9A illustrates a cross section view of a square embodiment of the lower portion of the replacement toothbrush head.

FIG. 9B illustrates a cross section view of a pentagonal embodiment of the lower portion of the replacement toothbrush head.

FIG. 10 illustrates a side view of an alternate embodiment of the toothbrush head assembly.

FIG. 11 illustrates a side view of an embodiment of a toothbrush head separator tool, e.g., a lever separator.

FIG. 12 illustrates a bottom view of the lever separator.

FIG. 13 illustrates a side view of the bushing.

FIG. 14 illustrates a bottom view of the bushing.

FIG. 15 illustrates a side view of an alternate electric toothbrush head assembly in the process of having the toothbrush head separated from the housing of the head assembly through use of a large bushing.

FIG. 16 illustrates one embodiment of the toothbrush head.

FIG. 17 illustrates an alternate embodiment of the toothbrush head.

FIG. 19 illustrates an embodiment of a toothbrush head separator tool, e.g., a double handle pull tool.

FIG. 20 illustrates an embodiment of a toothbrush head separator tool, e.g., a single handle twist pull tool.

FIG. 21 illustrates an embodiment of a toothbrush head separator tool, e.g., a pliers based separator.

DETAILED DESCRIPTION

An electric toothbrush head replacement system and method will now be described. In the following exemplary description numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

Figure 1:
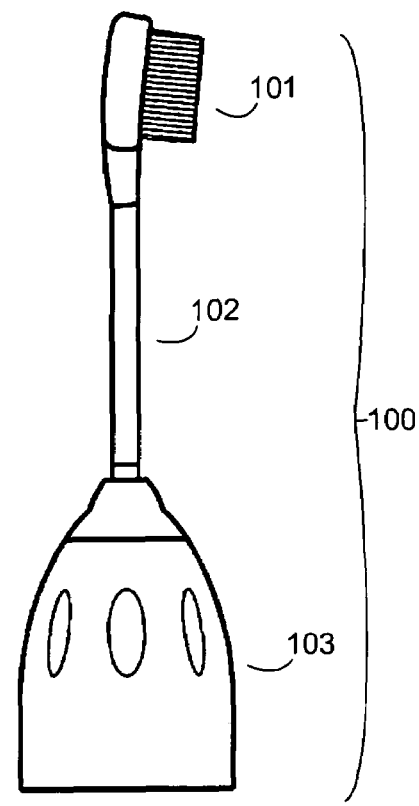
FIG. 1 illustrates a side view of an electric toothbrush head assembly.

FIG. 1 illustrates a side view of electric toothbrush head assembly 100. Electric toothbrush head assembly 100 includes toothbrush head 101, shank 102 and housing 103. Toothbrush head 101 after continued use becomes a worn toothbrush head having frayed bristles. To avoid replacing entire head assembly 100 when replacing toothbrush head 101, embodiments of the invention provide at least one toothbrush head separator tool that is configured to separate a worn toothbrush head from the shank or head assembly of an electric toothbrush. Embodiments of the invention also provide at least one replacement toothbrush head that couples with the shank or head assembly so that a new toothbrush head with new bristles is coupled with the electric toothbrush. One or more embodiments of the invention may utilize a toothbrush head shank adapter to couple with a replacement toothbrush head and the shank of the electric toothbrush (see FIG. 6 for example).

Figure 2:
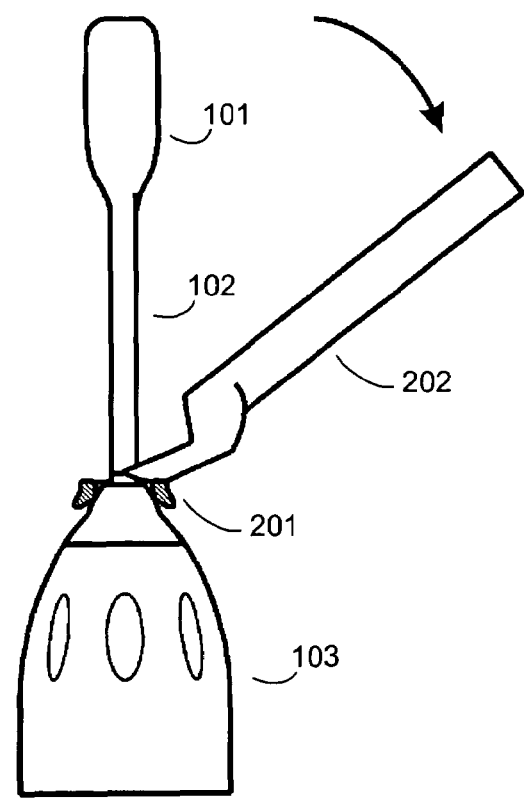
FIG. 2 illustrates a rear view of an electric toothbrush head assembly in the process of having the toothbrush head separated from the housing of the head assembly through use of a small bushing.

FIG. 2 illustrates a rear view of electric toothbrush head assembly 100 in the process of having toothbrush head 101 separated from housing 103 of head assembly 100 through use of a small bushing 201. Use of lever 202 which is an embodiment of the toothbrush head separator tool against small bushing 201 allows for toothbrush head 101 to be separated from housing 103 in this example.

Figure 3:
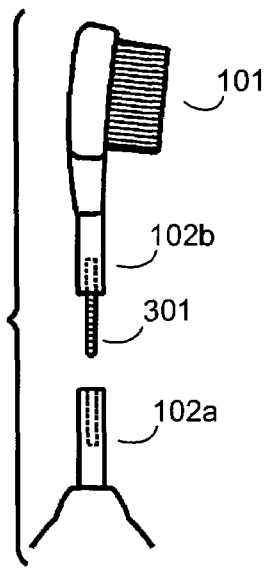
FIG. 3 illustrates construction of an embodiment of the shank wherein the shank uses an internal metal rod to couple the toothbrush head to the shank.

FIG. 3 illustrates construction of an embodiment of shank 102 wherein shank 102 uses internal rod 301, which may be metal in one or more embodiments of shank 102, to couple toothbrush head 101 to lower portion of shank 102a via shank 102b. When embodiments of the shank comprise internal rod 301, the portions of shank 102a and 102b may be separated using lever 202 shown in FIG. 2 or shank cutter 401 shown in FIG. 4.

Figure 4:
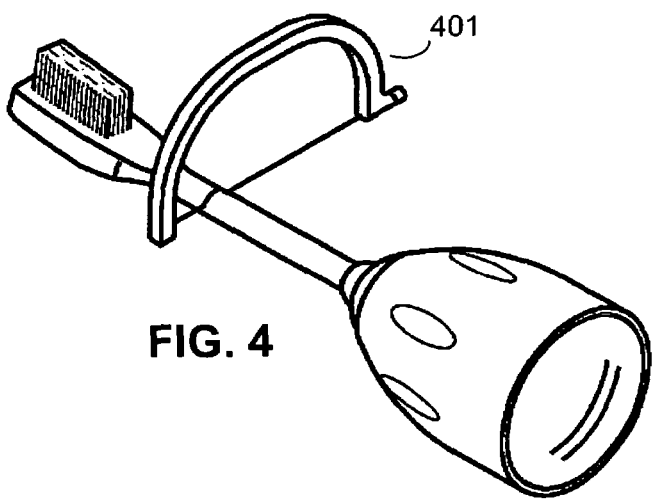
FIG. 4 illustrates a perspective view of an electric toothbrush head assembly in the process of having the toothbrush head separated from the shank of the head assembly with an embodiment of a toothbrush head separator tool.

FIG. 4 illustrates a perspective view of electric toothbrush head assembly 100 in the process of having toothbrush head 101 separated from the lower portion of the shank that couples with housing 103 through use of shank cutter 401. Any type of toothbrush head separator tool configured to separate a worn toothbrush head from the shank or housing of head assembly 100 so that the entire head assembly does not have to be replaced to replace a worn toothbrush head is in keeping with the spirit of the invention.

FIG. 5 illustrates an exploded perspective view of head assembly 100 with toothbrush head shank adapter 502 (or shank adapter for short) configured to hold replacement toothbrush head 501 on shank 102 of head assembly 100. In this embodiment of the invention, regardless of the initial type of coupling between toothbrush head 101 and shank 102, shank 102 is cut or the worn toothbrush head is removed from shank 102 so that shank adapter 502 may be introduced between shank 102 and replacement toothbrush head 501.

FIG. 6 illustrates a side view of the head assembly with a shank adapter configured to hold a replacement toothbrush head on the shank of the head assembly. Ridge 601 of replacement toothbrush head 501 fits into valley 602 of shank adapter 502 to secure replacement toothbrush head 501 to shank adapter 502. Shank adapter female port 603 couples with lower portion of shank 102a in order to secure shank adapter 502 to lower portion of shank 102a. Any type of bond or coupling between shank adapter female port 603 and lower portion of shank 102a is in keeping with the spirit of the invention. Forming shank adapter 502 may be performed by injection molding shank adapter 502 to fit a given manufacturer's electric toothbrush shank. Any other method of forming shank adapter 502 including machining is in keeping with the spirit of the invention. Forming replacement toothbrush head 501 or any other replacement toothbrush head described herewithin may also be accomplished by injection molding or any other type of manufacture so long as toothbrush head 501 includes a method for securing toothbrush head to housing 103 either via shank 102 or internal rod 301 or via any other method and as long as toothbrush head 103 may be utilized to brush one's teeth.

FIG. 7 illustrates a side view of shank adapter 502. Valley 603 may be manufactured in one or more embodiments to fit a particular make of electric toothbrush having a particular shank size. FIG. 8 illustrates a cross section view of a serrated embodiment of the lower portion of replacement toothbrush head 501. FIG. 9A illustrates a cross section view of a square embodiment of the lower portion of replacement toothbrush head 501. FIG. 9B illustrates a cross section view of a pentagonal embodiment of the lower portion of replacement toothbrush head 501. Any type of shape, including the hexagonal lower portion of replacement toothbrush head 501 as shown in FIG. 5 may be utilized as long as replacement toothbrush head is secure held in place so that it does not fail to rotate when used.

FIG. 10 illustrates a side view of an alternate embodiment of toothbrush head assembly. In this embodiment, toothbrush head assembly includes guard 1001. Shown in dotted lines is internal rod 301. FIG. 11 illustrates a side view of lever separator 202. FIG. 12 illustrates a bottom view of lever separator 202 including fork portion 1201. FIG. 13 illustrates a side view of bushing 1300. FIG. 14 illustrates a bottom view of bushing 1300. FIG. 15 illustrates a side view of an alternate electric toothbrush head assembly in the process of having toothbrush head 101 separated from housing 103 through use of bushing 1300 that allows for leverage to be applied between toothbrush head 101 and housing 103 of sufficient quantity to allow toothbrush head 101 to be separated from housing 103.

FIG. 16 illustrates one embodiment of toothbrush head 101a. FIG. 17 illustrates an alternate embodiment of toothbrush head 101b. Depending on the type of head assembly, replacement toothbrush head 100a or 101b may be utilized on toothbrush head assembly 1000 without shank adapter 502 for example. As long a replacement toothbrush head 101a, 101b or 501 securely rotate and maintains proper head vibration when coupled with housing 103, embodiments of the invention allow for replacement of worn toothbrush heads where no possibility existed.

Figure 18:
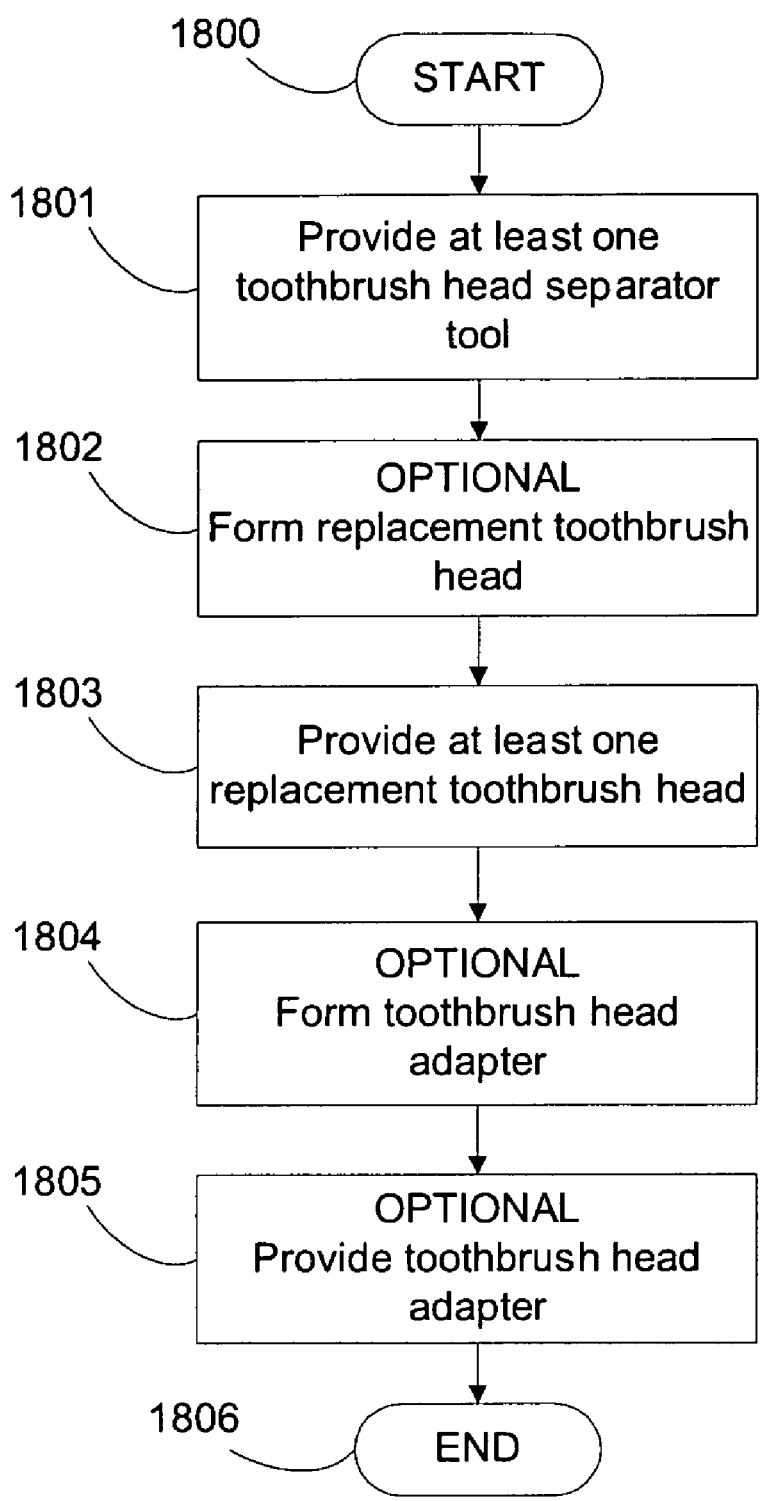
FIG. 18 illustrates a flow chart of an embodiment of the electric toothbrush head replacement method.

FIG. 18 illustrates a flow chart of an embodiment of the electric toothbrush head replacement method. Processing starts at 1800. At least one head separator tool is provided at 1801. A head separator tool may include a saw, a lever, a single or double handled pull tool, a pliers based tool or any other tool that may remove a toothbrush head from a head assembly of an electric toothbrush. Optionally, a replacement toothbrush head is formed at 1802. Injection molding or any other method of forming the replacement head is in keeping with the spirit of the invention. At least one replacement toothbrush head is provided at 1803. Electric toothbrush manufacturers that do not provide a method for replacement of worn toothbrush heads are candidate users of embodiments of the method described herein. Optionally, a toothbrush head adapter is formed at 1804. Again, any type of injection molding or machining may be used to form the optional toothbrush head adapter. Optionally, any toothbrush head adapter is provided at 1805. Processing ends at 1806. After processing ends a user may utilize the elements provided in order to replace toothbrush heads. Any method of coupling the replacement toothbrush head adapter or replacement toothbrush head to the head assembly is in keeping with the spirit of the invention. Any coupling for example may be glued or snapped on and may or may not be fluid tight.

FIG. 19 illustrates an embodiment of a toothbrush head separator tool, e.g., a double handle pull tool. By lifting both handles coupled to plunger 1091, toothbrush head 101 is removed by upward force. FIG. 20 illustrates an embodiment of a toothbrush head separator tool, e.g., a single handle twist pull tool. By twisting handle 2001, toothbrush head puller 2002 forces toothbrush head 101 away from head assembly 103 via separator body 2003. FIG. 21 illustrates an embodiment of a toothbrush head separator tool, e.g., a pliers based separator. In this embodiment, fork portion 1201 is moved away from lower fork 2102 that couples with a toothbrush head assembly to remove a toothbrush head when handle 2101 is depressed. Any other type of toothbrush head separator tool in addition to those illustrated herein that are capable of removing a toothbrush head from a head assembly are in keeping with the spirit of the invention.

While the invention herein disclosed has been described by means of specific embodiments and applications thereof, numerous modifications and variations could be made thereto by those skilled in the art without departing from the scope of the invention set forth in the claims.

What is claimed is:

1. A system for electric toothbrush head replacement comprising:
   at least one non-cutting toothbrush head separator tool configured to separate a worn toothbrush head from a head assembly of an electric toothbrush having a shank for holding said worn toothbrush head;
   at least one replacement toothbrush head configured to couple with said head assembly of said electric toothbrush; and
   a toothbrush head adapter configured for coupling said at least one replacement toothbrush head to said shank.

2. The electric toothbrush head replacement system of claim 1, wherein said at least one non-cutting toothbrush head separator tool comprises a forked lever configured to separate said worn toothbrush head from said head assembly.

3. The electric toothbrush head replacement system of claim 2, wherein said at least one non-cutting toothbrush head separator tool further comprises a bushing configured to allow said forked lever to exert a force on said bushing that in turn exerts said force on a housing, wherein said force is sufficient to separate said head from said head assembly.

4. The electric toothbrush head replacement system of claim 2, wherein said forked lever is configured to fit around an internal metal rod in said shank.

5. The electric toothbrush head replacement system of claim 1, wherein said at least one non-cutting toothbrush head separator tool comprises a pulling apparatus configured to separate said worn toothbrush head from said head assembly.

6. The electric toothbrush head replacement system of claim 5, wherein said pulling apparatus comprises a screw mechanism.

7. The electric toothbrush head replacement system of claim 5, wherein said pulling apparatus comprises a mechanism having at least one pivot.

8. A method for electric toothbrush head replacement comprising:
   providing at least one non-cutting toothbrush head separator tool configured to separate a worn toothbrush head from a head assembly of an electric toothbrush having a shank for holding said worn toothbrush head;

providing at least one replacement toothbrush head configured to couple with said head assembly of said electric toothbrush; and providing a toothbrush head adapter configured for coupling said at least one replacement toothbrush head to said shank.

9. The electric toothbrush head replacement method of claim 8, wherein said step of providing said at least one non-cutting toothbrush head separator tool comprises providing a forked lever configured to separate said worn toothbrush head from said head assembly.

10. The electric toothbrush head replacement method of claim 9, wherein said step of providing said at least one non-cutting toothbrush head separator tool further comprises providing a bushing configured to allow said forked lever to exert a force on said bushing that in turn exerts said force on a housing, wherein said force is sufficient to separate said head from said head assembly.

11. The electric toothbrush head replacement method of claim 9, wherein said forked lever is configured to fit around an internal metal rod in said shank.

12. The electric toothbrush head replacement method of claim 8, wherein said step of providing said at least one non-cutting toothbrush head separator tool comprises providing a pulling apparatus configured to separate said worn toothbrush head from said head assembly.

13. The electric toothbrush head replacement method of claim 12, wherein said pulling apparatus comprises a screw mechanism.

14. The electric toothbrush head replacement method of claim 12, wherein said pulling apparatus comprises a mechanism having at least one pivot.

* * * * *